Figure 1:
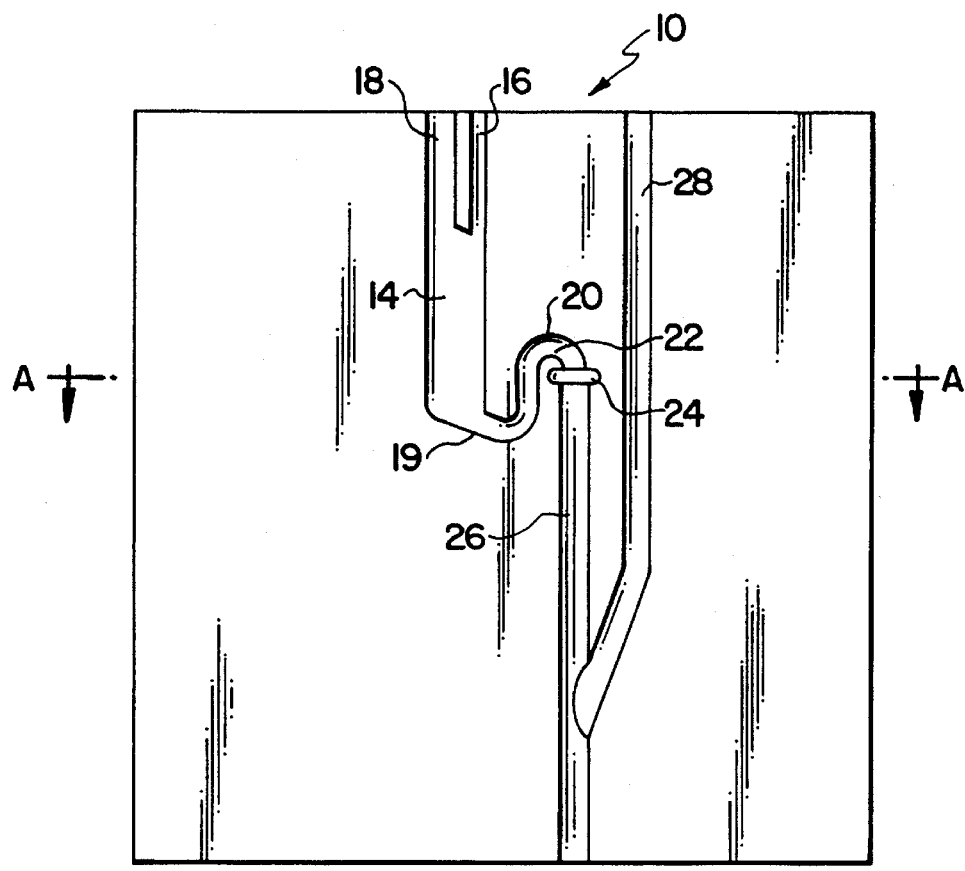

United States Patent [19]

Dietz et al.

[11] Patent Number: 5,483,830
[45] Date of Patent: Jan. 16, 1996

[54] METHOD AND APPARATUS FOR MEASURING A LIQUID FLOW USING A SIPHON UNIT AND AN AERATING DUCT

[75] Inventors: Xaver Dietz, Vohburg; Georg Kothmeier, Ingolstadt, both of Germany

[73] Assignee: Durango holding GmbH, Ingolstadt, Germany

[21] Appl. No.: 108,608

[22] PCT Filed: Feb. 5, 1992

[86] PCT No.: PCT/EP92/00499

§ 371 Date: Dec. 8, 1993

§ 102(e) Date: Dec. 8, 1993

[87] PCT Pub. No.: WO92/15249

PCT Pub. Date: Sep. 17, 1992

[30] Foreign Application Priority Data

Mar. 5, 1991 [DE] Germany ............ 41 06 995.1

[51] Int. Cl.[6] .................................... G01F 3/38
[52] U.S. Cl. ........................................... 73/226
[58] Field of Search ............ 73/223, 226; 128/760, 128/761

[56] References Cited

U.S. PATENT DOCUMENTS

| 2,069,677 | 2/1937 | Ollagnon | 73/226 |
| 3,919,455 | 11/1975 | Sigdell et al. | 73/226 |
| 4,589,280 | 5/1986 | Carter | 73/226 |
| 4,619,273 | 10/1986 | Iosif | 128/771 |
| 4,683,748 | 8/1987 | Carter | 73/226 |

FOREIGN PATENT DOCUMENTS

| 2253033 | 5/1974 | Germany. |
| 3544676 | 7/1986 | Germany. |
| 3500895 | 7/1986 | Germany. |
| 2031158 | 4/1980 | United Kingdom. |

Primary Examiner—Richard E. Chilcot, Jr.
Assistant Examiner—Harshad Patel
Attorney, Agent, or Firm—Keck, Mahin & Cate

[57] ABSTRACT

The invention provides a measuring apparatus for measuring small liquid flows, particularly in the medical sector. The measuring apparatus comprises a siphon unit as a liquid flow sensor, a measuring chamber being located in its retention area. As soon as the liquid supplied to the measuring chamber reaches a given liquid level, the measuring chamber is automatically emptied by the siphon effect. The emptied liquid volume is fixed and constant. The emptying is determined by an optical detector means in the vicinity of the measuring chamber and/or upstream of the outflow area of the siphon unit.

18 Claims, 5 Drawing Sheets

METHOD AND APPARATUS FOR MEASURING A LIQUID FLOW USING A SIPHON UNIT AND AN AERATING DUCT

The invention relates to a method and a apparatus for measuring a liquid flow.

In the laboratory field and, in particular, in the medical field there is a need to be able to measure small volume flows of liquids in a very accurate manner. Certain problems occur more particularly in the clinical field.

The liquids to be measured are on occasions chemical-aggressive body fluids, which are inter alia mixed with solids, e.g. protein. For the measurement of such fluids, a simple measuring apparatus construction is necessary, offering minimum attack surfaces to the impurities. This simple construction is also opposed by the high hygienic requirements of a clinical department.

A number of different principles are known for the determination of the volume of a liquid flow, particularly in the case of urine meters.

A method and an apparatus according to the invention of the above-mentioned type are known from U.S. Pat. No. 4,619,273.

The method and apparatus known therefrom are primarily designed for determining the discharge speed of a urine-discharging patient and for determining also the quantificated amount of the discharged liquid by means of a subsequent siphon arrangement.

This method and the apparatus are therefore designed for the spontaneous discharge of a relatively large volume of a liquid. As a result of this high flow rate, air is sucked in relative to the through-flowing liquid via the aerating duct, which is annularly arranged around the filling duct and is in connection with its surroundings, whereby air bubbles are produced for separating individual liquid volumes from each other. In case this apparatus was used for determining the volume of very small discharged volumes, as those that occur in the case of patients which have been provided with a bladder catheter, a liquid discharge of a kind of a dripping film would occur in the lower rounding of the siphon discharge area, which is positioned in a horizontal plane with the upper rounding of the inlet area, when this horizontal level is reached, as a result of the geometrical design of the siphon arrangement. This, however, does not allow a defined determination of the outflowing volume and by no means the forming of equally-sized measuring volumes.

Thus, it is the object of this reference to disclose that the apparatus described is suitable for measuring high liquid flows and that only here the measuring method functions. Due to the effect of a liquid stopper in the discharge tube, the corresponding amount of liquid is sucked out of the siphon.

In the case of a slow liquid flow, this stopper would dissolve, dripping along the walls of the siphon, so that the suction effect and consequently also the function of the measurement determination would be lost.

Further, a measuring apparatus is known in U.S. Pat. Nos. 4,683,748 and 4,589,280) which is designed for receiving a larger measurement volume of discharged urine. From the corresponding measuring chamber, a pressure duct passes upwards from the base and is terminated by a transducer detecting the analog values of the pressure rise. These analog values can then be converted by means of an electronic evaluating circuit into the measuring chamber filling level and, therefore, into the measurement volume.

In order to avoid a undesired retention of the discharged urine and so as to exclude any contamination, said measuring apparatus also has an overflow in the manner of a siphon, whose intake duct starts well above the lowest level of the measuring chamber. The function of this known siphon arrangement can therefore be looked upon as a purely overflow function, which as a result of a partial emptying of the measuring chamber brings about a corresponding pressure difference for the transducer.

In said measuring apparatus the complicated construction of the electronic evaluating device is problematical and the analog determination of the indirect parameter of the pressure can give rise to significant errors. In addition, sediments which are washed out with the urine are deposited in the measuring chamber without said sediments also being flushed out. This gives rise to an imprecision of the measured result.

In another known measuring apparatus (DE 3 544 676 A1) parameters of the delivered liquid flow, such as specific weight, temperature, etc., are calculated by means of a relatively complicated measuring chamber arrangement with following electronic evaluating device. This measuring apparatus is mainly intended for the continuous determination of qualitative parameters of urine liquid flow. The siphon arrangement mentioned in this connection is used solely for determining specific parameters in separate, individual liquid volumes, without any mixing taking place. However, the liquid flow volume is determined by means of a weight measurement of the liquid flow passing through by means of strain gauges.

However, due to its complexity, such a measuring apparatus is highly error-prone, which more particularly applies to the weight and consequently also volume determination of the liquid flow.

U.S. Pat. No. 3,919,455 (FIG. 1) also discloses a measuring apparatus, into whose cylindrical container projects a U-tube with its opening pointing downwards. This container is filled, without detectable aerating and deaerating lines, with liquid until the top level of the U-shaped siphon is exceeded. At this time the siphon function comes into action and the relatively large volume is emptied from the container to the lowest level of the U-tube. In the case of complete filling of the filling duct through the supplied liquid, the omission of aeration and deareation can lead to a rising air pressure in the container, which initiates the siphon function well before the top liquid level is reached, so that different measuring volumes in the discharge channel or duct are digitally determined.

The measuring apparatus known from GB 2 031 158 A1 operates in the same way.

It is considered disadvantageous in the two last mentioned measuring apparatuses, that there is no complete emptying of the measuring chamber and as a result of the distance between the lower suction opening and the bottom of the measuring chamber, a residual volume is left behind in the latter. However, the smaller the spacing or distance, the more the liquid outflow is decelerated by the suction tube, because the flow rate is impaired by the narrowiing gap.

However, further disadvantages are associated with this. The ever decreasing discharge speed also leads to a measuring inaccuracy, because during the digitally determined, relatively slow liquid outflow further liquid flows from above into the filling duct from the suction tube and this is consequently also included in the measuring volumes. Thus, this wipes out the exact proportioning important for digital determination.

Another disadvantage is the reduced capacity of this siphon to entrain sediments located in the liquid or which have deposited on the bottom of the measuring chamber.

In addition, turblence at the lower edges of the siphon tube, which impairs optimum aerohydrodynamics. There are also relatively large measuring volumes in said measuring chamber and as a result of the large surfaces wetted different flow characteristics and therefore errors occur.

It can also be looked upon as disadvantageous that with a slightly inclined position of the known measuring arrangements air is also sucked towards the end of the suction process, which leads to an air/liquid mixture and can give rise to incorrect counts in the digital, electronic measuring apparatus, because there is no clearly defined, terminating liquid meniscus.

It is also problematical in such known measuring apparatuses, particularly having a large wetting surface in the measuring chamber, that the wetting behavior of the liquids on surfaces has a mathematically not precisely describable hysteresis, i.e. behaves in a stochastic manner. In particular the adhesive power of the liquid on the wall has a significant influence and can therefore not be calculated in advance. Thus, in the case of such measuring apparatuses there are significant variations of the individual measuring volumes, which obviously have a negative on the accuracy of the digital determination.

Thus, the known measuring apparatuses have high inaccuracies with respect to the individual measuring volumes. The apparatuses are normally relatively complex and therefore involve comparatively high costs. As a result of large surfaces in the measuring chambers additional problems occur, which also give rise to a high tilting or inclination sensitivity.

The object of the invention is therefore to provide a method and a relatively simple and inexpensive apparatus for measuring the volume of liquid flow, which is more particulary usable in the clinical sector, e.g. in intensive care units and which permits a functionally reliable and precise measurement of the liquid flow.

An important basic concept of the invention is the geometrical design of the siphon unit, which makes it possible to quantify the liquid flow which has flown in in substantially identical measuring volumes and enables the determination of the presence or outflow and emptying of the measuring volume by means of a unit step response of the detector means, which correspondingly takes place in pulse-like, digital manner. Thus, by means of the vary small, clearly defined and individual measuring volume and the number of traversed measuring volumes, the total volume of the liquid flow can be precisely evaluated in a time-dependent manner.

The invention is therefore based on the basic principle of closely juxtaposing the siphon and the measuring chamber and if possible to construct the same in the manner of a tube or tube widening or extension, so as to obtain small identical volumes as the individual measuring volumes.

The continuous transfer between the measuring chamber and the siphon, whilst appropriately providing a base slope towards the siphon, permits optimum flow conditions, so that emptying can take place very rapidly.

The internal diameter of the siphon and the measuring chamber, particularly for urine measurement, is fixed at a diameter of min. approximately 4 mm, so that sediments can be entrained during the outflow of the individual measuring volumes. In view of the liquid and its viscosity, the siphon diameter must be made so small that a clearly defined liquid meniscus can form. Account must obviously also be taken of the material hydrophoby end of the fact that no capillary effects must occur.

Thus, since according to the invention edges and sharp curvature radii are to be avoided and an approximately constant flow cross-section is present in the measuring chamber and siphon, at the end of each measuring cycle a precisely defined liquid meniscus can be formed, which also permits a precise digital count. Independently of the inclination of the unit about an axis perpendicular to the plane of symmetry thereof, a clear end meniscus always formed.

In order to further improve precision in connection with the measuring volumes, advantageously the electronic detector device eliminates influences with respect to the inclination of the siphon unit and the flow quantity.

Thus, according to the invention from the bottom of the measuring chamber a tube connected to the siphon passes in nozzle-like manner to the latter and enters said siphon. The tube cross-section roughly corresponds to that of the siphon. There is also a gradient from the bottom of the measuring chamber to the siphon intake. The inlet of the measuring chamber is formed by a relatively small diameter filling tube, so that also in the case on an inclined position and slope of the siphon unit there can only be a very limited volume error, which can be detector-eliminated.

The measuring apparatus according to the invention is also characterized in that the siphon is positioned externally with respect to the measuring chamber and the emptying process of the measuring chamber, which is in particular constructed as a pipe or tube widening, takes place from below. There are homogeneous curves in the measuring chamber and siphon, so that the edges which are prejudicial to the aerohydrodynamics are avoided. The measuring chamber is appropriately designed as a tube widening and this can e.g. be conical, sperical or in the form of an oval ellipsoid of revolution.

The filling duct to the measuring chamber is preferably constructed as an inclined duct and its diameter can be smaller than that of the measuring chamber.

For the favourable influencing of the outflow characteristics, the outflow duct is inserted in sloping cut manner in the back flow duct and a trumpet-shaped widening can also be provided.

For the definite formation of a liquid meniscus a diameter jump can be provided behind the top siphon level. In comparable manner there can also be a diameter jump at the transition from the filling duct to the measuring chamber.

Advantageously an internal aeration and deaeration is chosen, which is supplied from the area of the outflow duct over the highest siphon level upstream and downstream of the measuring chamber.

With a view to an optimum monitoring the siphon unit is made from a transparent plastic. this is appropriately formed from two substantially identical half-blocks, which are injection moulded and which can be tightly interconnected e.g. by ultrasonic welding, bonding or screwing. The corresponding material is appropriately hydrophobic. The complete siphon unit can therefore be constructed in the manner of a disposable article. So as to be less prejudicial to the environment it is also possible to use a biodegradable or rottable plastic, e.g. Biocellat (trademark of the Battelle Institut, Frankfurt a.M.), and a cellulose diacetate can be used as the basic material and is mixed with plasticizers. Other vegetable oil-based plastics can also be used from the injection moulding standpoint.

In a further simplified form within guide pins of the plastic half-blocks is inserted a transparent plastic hose, which forms the supply duct, measuring chamber, siphon and outflow duct. Upstream of the supply duct and downstream of the outflow duct filters are used in this case and they vent the interior of the hose.

The advantage of this embodiment is that only the hose has to be replaced and can be looked upon as a disposable article, whereas the two plastic half-blocks are reusable.

The electronic detector means preferably has correlation devices for eliminating measuring errors due to inclinations of the siphon unit and due to different flow volumes.

The design of the actual siphon unit, linked with the step of a simple digital determination of the outflow or presence of the individual measuring volumes, consequently allows an inexpensive, precisely functioning measuring apparatus, which can e.g. as a result of the indirect optical determination of the individual measuring volumes can be used in industry, chemistry, environmental engineering or the clinical sector independently of the aggressiveness or contamination possibility of the liquid flow.

As a result of the preferred orientation of a reflected light barrier in a measuring chamber located in the retention area of the siphon unit, the number of emptying or siphon cycles is precisely determined. A measurement can also take place in the outflow area of the siphon unit.

In order to be able to carry out a very precise volume flow measurement, it is desirable to accurately define the volume in the measuring chamber of the siphon unit. An exact fixing of the measuring volume in the measuring chamber can take place if the siphon has a diameter jump in the vicinity of the overflow edge. In the case of liquid retention in the measuring chamber, as a result of the surface tension of the liquid, a diaphragm or membrane forms at this diameter jump. The measuring chamber is then emptied when the height of the retained liquid in the measuring chamber exceeds the surface tension of this membrane. This is a clearly defined release point as compared with conventional siphon units, where the liquid, as a function of the surface tension, is retained or builds up to above the overflow edge and a premature release can take place through turbulence due to inflowing liquid or due to minor position changes of the siphon unit.

The liquid flow conditions in the siphon unit decisive for initiating emptying and for the actual emptying can also be improved if the siphon unit is made from a hydrophobic material and/or undergoes a hydrophobic treatment.

In order to obtain a limited dependence of the measuring volume on the position of the siphon unit, it is also advantageous to provide a riser directed upwards from the measuring chamber with a small diameter, because the earlier or later initiation of the emptying process due to a rotation or tilting of the siphon unit would lead to smaller volume differences in the measuring chamber due to the smaller riser radius. The measuring chamber should then be filled by means of a separate filling duct with a smaller diameter into the measuring chamber, because a filling via the riser with the smaller diameter could lead to the formation of air inclusions. The filing duct diameter must be sifficiently small that due to the resulting large capillary forces the liquid volume present therein does not participate in the emptying process. For this reason the filling duct also advantageously issues from the bottom into the measuring chamber.

In the horizontal plane the siphon should be juxtaposed as closely as possible with the riser, in order to increase the positional insensitivity of the measuring apparatus. The earlier or later initiation of the emptying due to a tilting or slope of the siphon unit also here leads to smaller differences of the liquid volume in the measuring chamber or in the riser.

For avoiding excessive capillary forces in the measuring chamber, the latter should have a diameter of at least 4 mm. However, the outflow diameter should be somewhat smaller, because otherwise the automatic emptying of the siphon unit resulting from the capillary action and the cohesive action of the liquid is no longer reliably ensured.

The siphon unit is advantageously made from transparent plastic, e.g. a polyacrylic material, in order to facilitate the coupling of the reflected light barrier to the detector means.

As a function of the medium of the liquid flow and the material from which the siphon unit is made, it would be appropriate to use detector means based on infrared, ultrasonic or electrostatic action. It is also possible to have a detector means for determining the magnetic field change between present and absent measuring volumes. It is here again possible to maintain the basic principle of an indirect measurement, which does not come into direct contact with the liquid flow and a unit pulse or step response, which permits the digitally simple determination of the number of measuring volumes.

The measuring apparatus is more particularly suitable for liquid measurements in the clinical sector and more specifically for urine measurements. The measuring apparatus permits an automatic measurement and monitoring of continuous urine discharges, particularly of patients in intensive care units. Since the measuring method leads to a digital signal, the information obtained can be used in a very satisfactory manner for a time and/or static evaluation.

The measuring apparatus can be used for a flow band width of 5 ml/h to 3 l/h with a measuring precision of approximately 2% or lower.

Although the measurement by means of a volume flow sensor according to the siphon principle is subjected to the most varied parameters of the liquid and the flow geometry of the siphon unit, very accurate measured results are obtained, which are not significantly influenced by protein coagulations and other contaminants, such as e.g. very small blood clots.

With a view to a complete emptying of the siphon unit, including the measuring chamber, the siphon unit is preferably attached at the bottom level, which advantageously slopes downwards, so that short-term sediment deposits are also rinsed out during the next emptying process.

The siphon unit can be manufactured as a flow sensor in the form of a disposable article. There is no need for movable parts or electrical connections. Therefore the measuring apparatus satisfies the requirements made with regards to inexpensiveness, operational reliability and hygiene made on equipment in the clinical sector. With this apparatus there is no need for the hitherto necessary reading off of the urine quantity on a micturition bag, which is associated with a risk of reading and transmission errors. Therefore the invention offers assistance in connection with the critical personnel problem in the hospital sector, because nurses are freed from these easily automated, manual activities and can devote themself more intensely to patient care.

The measuring apparatus is eminently suitable for the automatic monitoring of the kidney function, e.g. in an intensive care unit. Thus, the detected signal can e.g. be compared with a reference signal and can give to an automatic alarm if, for certain time, there is a drop below or rise above a specific delivery quantity.

Thus, through the smallest possible portioning of the liquid volumes to be measured, the invention leads to maximum accuracy. From the manufacturing standpoint as a result of the simple design without any undercuts a mass produced article is obtained with relatively low manufacturing costs.

Although the description has mainly been directed at urine quantity measurement, the measuring apparatus can obviously also be used for blood measurements, flow determination of infusions, as well as in other fields, e.g. in the determination of precipitation caused by rainwater or the measuring of leaks in the chemical or nuclear fields.

The invention is described in greater detail hereinafter relative to non-limitative embodiments and the attached drawings, wherein show:

FIG. 1 a longitudinal section through a siphon unit with a limited variance of the filling level.

Figure 2:
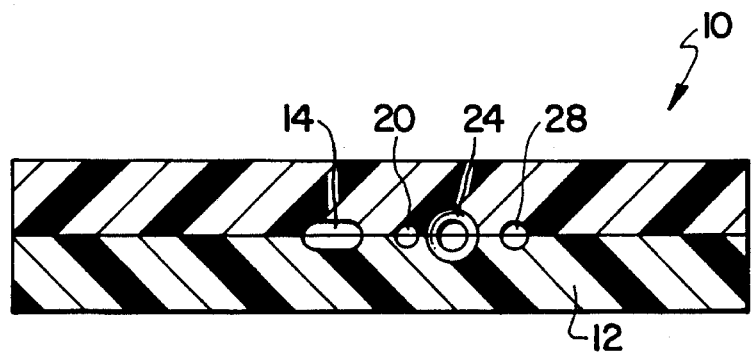

FIG. 2 section A—A from FIG. 1.

Figure 3:
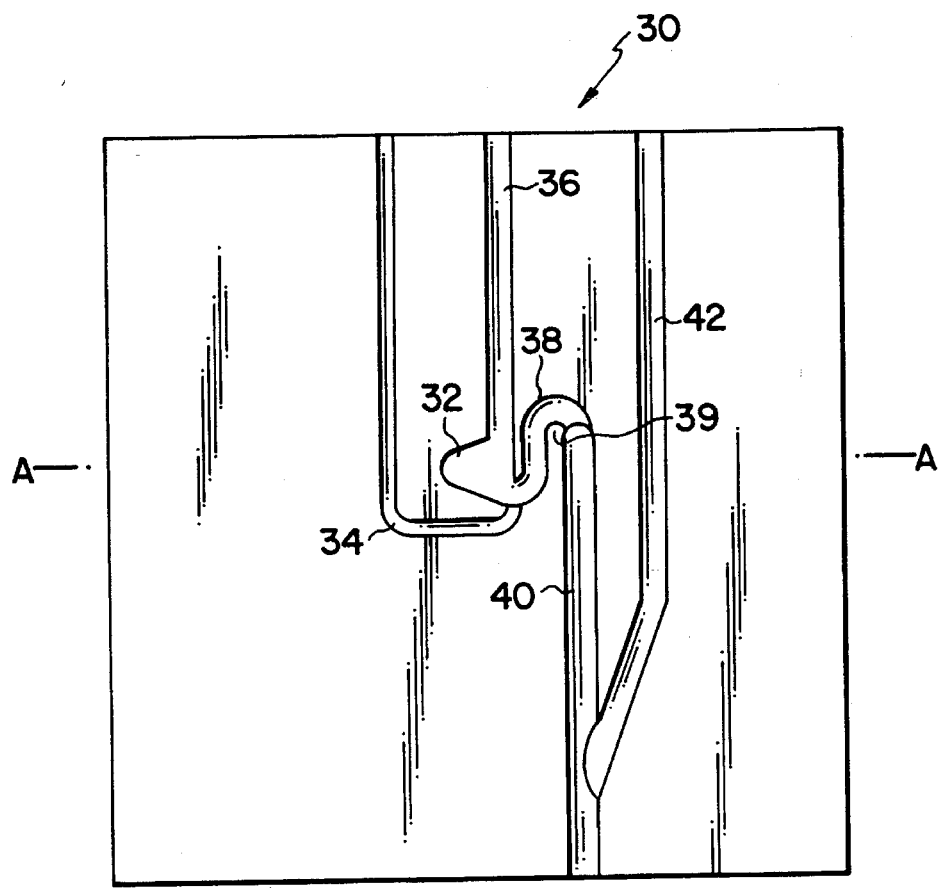

FIG. 3 a longitudinal section through a siphon unit with measuring chamber filling from below.

Figure 4:
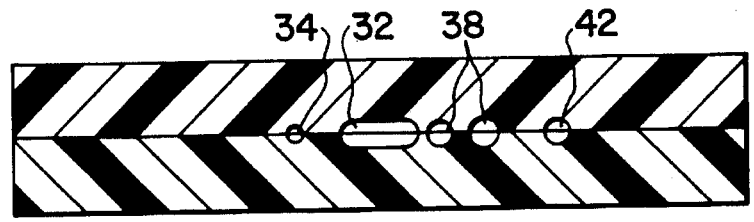

FIG. 4 the section A—A from FIG. 3.

Figure 5:
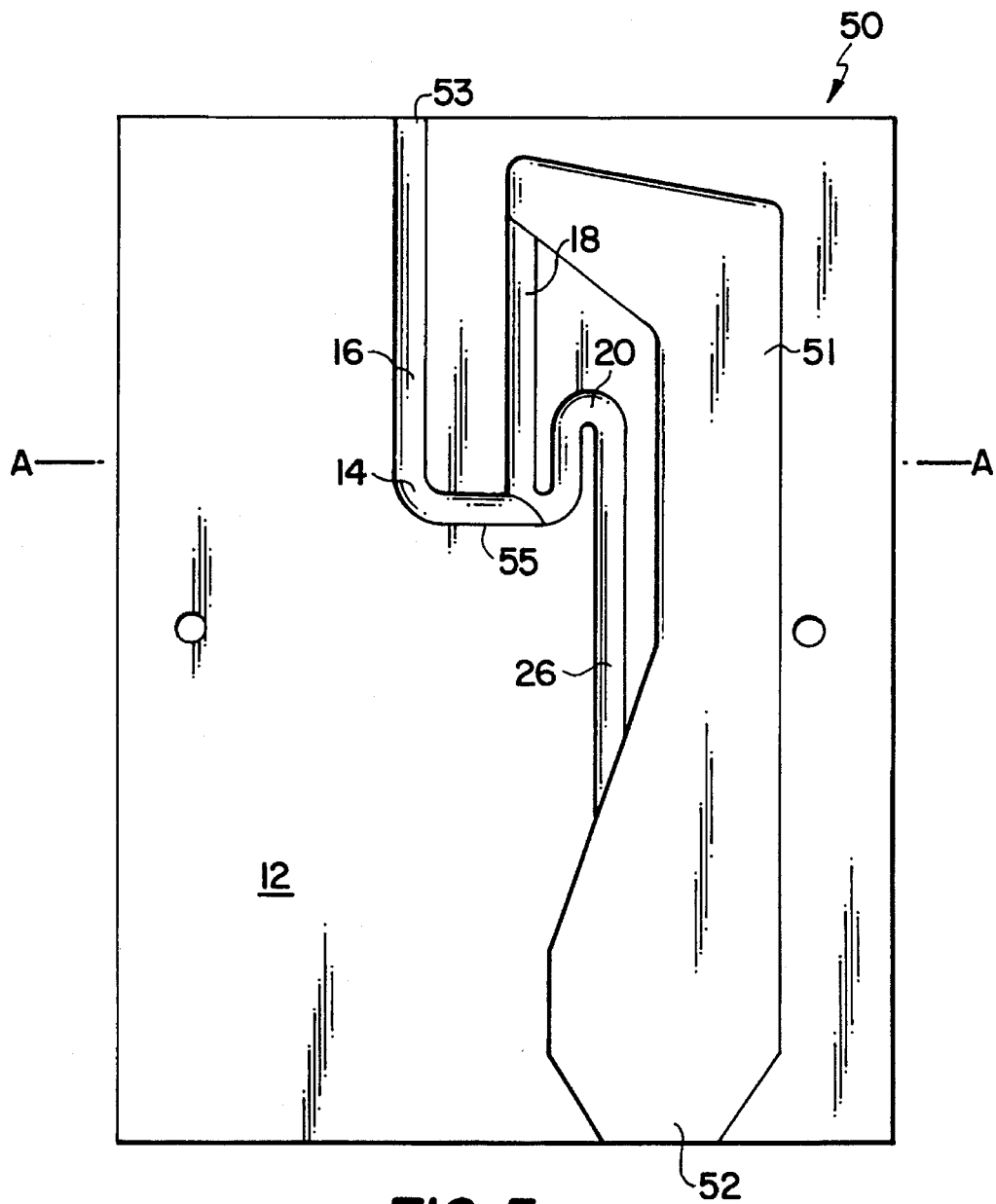

FIG. 5 a longitudinal section through a further embodiment of a siphon unit.

Figure 6:
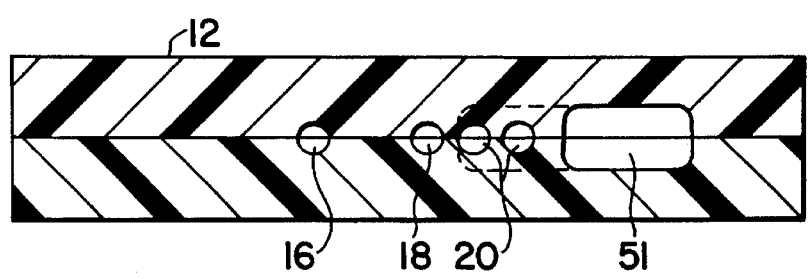

FIG. 6 the cross-section A—A of FIG. 5.

Figure 7:
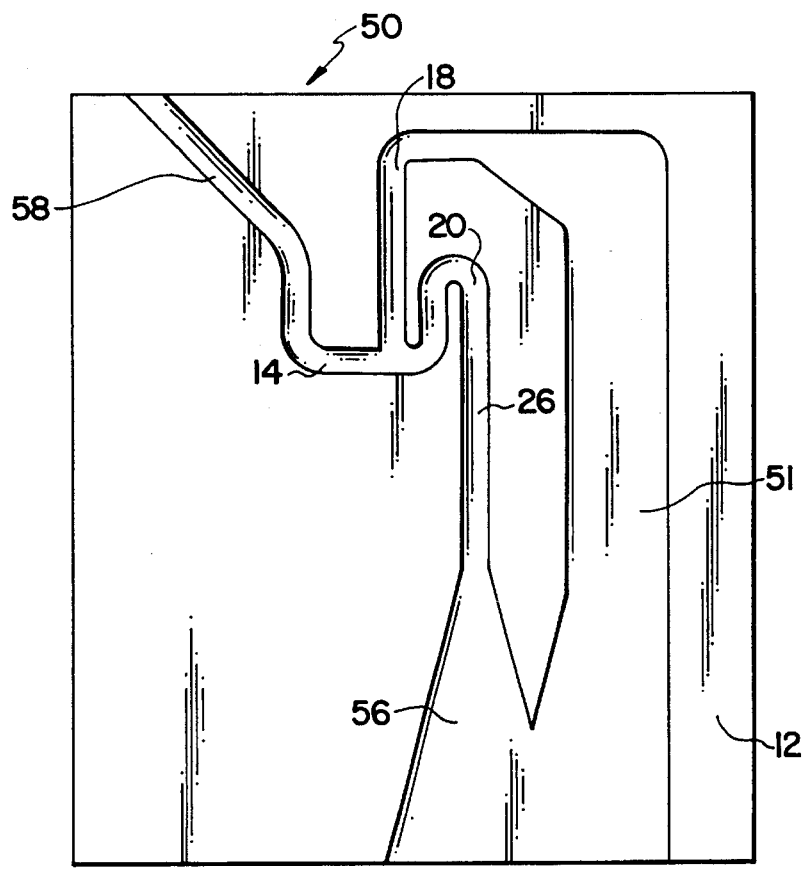

FIG. 7 a diagrammatic longitudinal section through a further embodiment of a siphon unit with a trumpet-like widened outflow duct.

Figure 8:
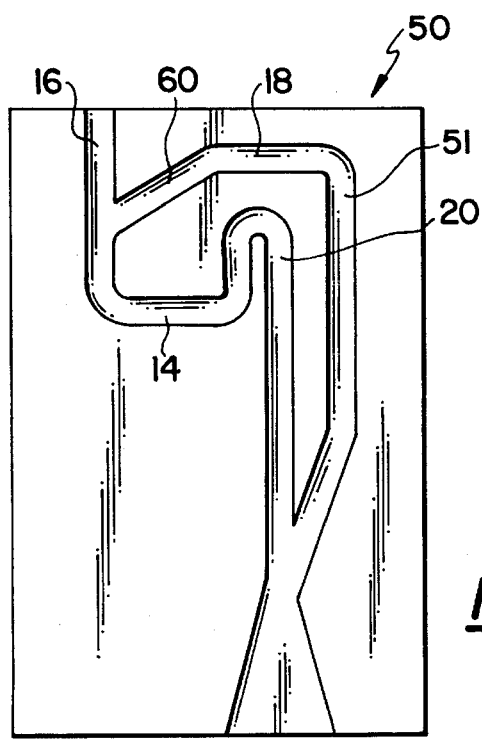

FIG. 8 a longitudinal section through a further embodiment of a siphon unit with a back flow duct returned from the discharge or outflow duct in the area upstream of the measuring chamber.

Figure 9:
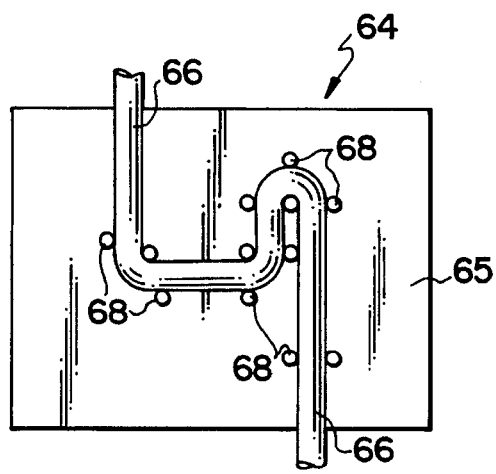

FIG. 9 another embodiment od a siphon unit in longitudinal section, in which the measuring chamber and the siphon are formed by a hose inserted between guide pins.

Figure 10:
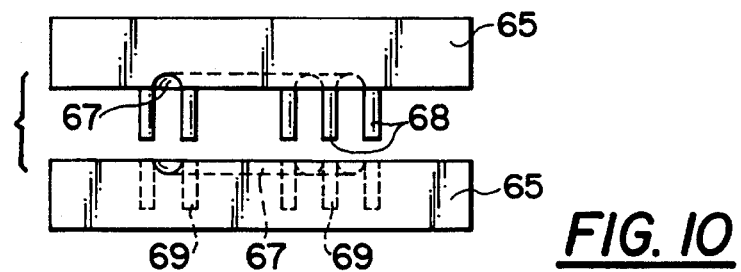

FIG. 10 a diagrammatic plan view of the two halves of the siphon unit according to FIG. 9 in the phase of joining together, but without hose insertion.

Figure 11:
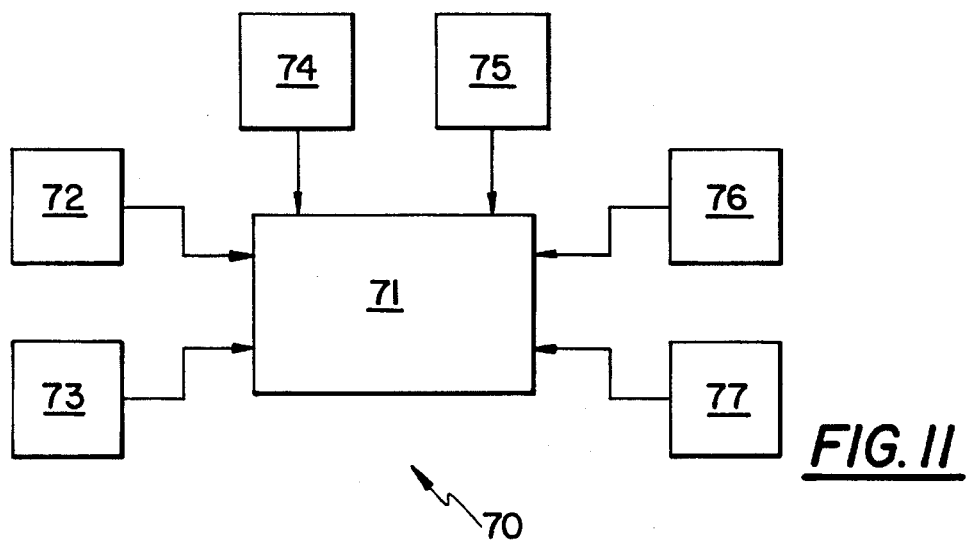

FIG. 11 a diagrammatic block view of a detector means with correlation units for taking account of the through-flow and inclination.

FIG. 1 shows a siphon unit 10 in a polystyrene block 12 as a sensor means e.g. for urine measurements in hospitals. Appropriately said siphon unit 10 comprises two half-blocks constructed in homologous manner to the cental sectional plane and which can e.g. be sealingly screwed together, so that it is easy to manufacture even relatively complicated contours of the siphon unit 10. In the retention area of the siphon unit 10 there is a measuring chamber 14, into which issue from above a filling duct 16 and a venting or aerating duct 18. The measuring chamber 14 passes continuously into the S or sinusoidal siphon 20 by means of a bottom level 19 sloping away at least slightly towards said siphon 20. Downstream of the upper overflow edge 22 of the siphon 20 the outflow has a diameter jump 24. Following said diameter jump 24 the outflow is formed by a vertical outflow duct 26 having a larger diameter than the siphon 20. At an acute angle, a second aerating duct 28 issues into the outflow duct 26 and it can be connected to the first aerating duct 18 for the measuring chamber 14 or to the ambient atmosphere.

FIG. 2 shows a section through the polystyrene block 12 at point A—A. This section illustrates the diameter conditions of different areas of the siphon unit 10.

The operation of the liquid flow sensor will now briefly be described. By means of the filling duct 16 the measuring chamber 14 is filled with liquid in the retention area of the siphon unit 10 in accordance with the liquid flow to be measured, the liquid rising in the siphon 20. The liquid rises corresponding to the filling level in the measuring chamber 14 to above the upper overflow edge 22 of the siphon 20 and at the diameter jump 24 forms a liquid membrane. In the case of further liquid rising in the measuring chamber 14, for a clearly defined filling level, the surface tension of the liquid membrane at the diameter jump 24 is exceeded and all the liquid in the measuring chamber 14 is, as a result of its cohesive effect, abruptly and substantially completely emptied through the siphon 20 and the outflow duct 26. This emptying is measured by means of a not shown reflected light barrier, preferably located in the vicinity of the measuring chamber 14 or optionally in the outflow duct. Thus, a signal is obtained for each emptying cycle and as a result of the clearly defined filling volume of the measuring chamber provides precise information on the flow rate through the sensor 10 constructed as a siphon unit.

FIGS. 3 and 4 show a further embodiment of a siphon unit 30, which has a measuring chamber 32, which is filled from the bottom by means of a filling duct 34 which has a smaller diameter than the siphon 38. Into the measuring chamber 32 issues from above a riser 36 with a smaller diameter than the width of the measuring chamber 32. From the bottom of the measuring chamber 32 the siphon-like outflow 38 leads into a vertical outflow duct 40, into which issues at an acute angle an aerating duct 42, which is connected to the atmosphere or the riser 36. The advantage of this siphon unit 30 is that the filling volume of the measuring chamber 32 does not differ significantly in the case of a slight inclination of the siphon unit 30 about a horizontal axis. In this siphon unit 30 the emptying process is initiated if the liquid rises above the upper overflow edge 39 of the siphon 38. A rotation of the siphon unit 30 about an axis projecting out of the drawing plane leads to an earlier or later initiation of the emptying process compared with the unpivoted position and the liquid level in the riser 36 is somewhat higher or lower on initiating emptying. This filling level difference during emptying only leads to a minor change in the liquid volume in the overall measuring chamber 32, because compared with the latter the riser 36 has a small diameter and consequently a liquid level difference in the riser only leads to a small absolute volume difference. The smaller riser diameter 36 makes it necessary for its own filling duct 34 to issue into the measuring chamber 32. Compared with the outflow 38 the filling duct 34 has a small diameter, so that the liquid volume in said duct 34 does not participate in the emptying process. In the horizontal plane the siphon 38 is very close to the riser 36, so as to keep as small as possible the difference of the position-dependent liquid level in the riser 36 on initiating emptying.

FIG. 5 shows another embodiment of a siphon unit 50 in a play view of the lateral face of a half-shell block 12 made from transparent plastic.

The siphon 20, which is constructed in S, sinusoidal or U-shaped manner, passes on one side into a vertically arranged outflow duct 26. On the inflow side the siphon unit 50 has a single inflow opening 53, which in the present embodiment ends at the upper edge of the block 12. From said inflow opening 53 the filling duct 16 leads vertically downwards and its lower part forms part of the measuring chamber 14. In the embodiment according to FIG. 5 the measuring chamber 14 is consequently formed by a circular or oval duct, which has approximately the same diameter as the duct of the siphon 20. Considered geometrically the measuring chamber 14 is formed by an approximately horizontal duct 55, which in the left-hand area passes in continuously curved manner into the filling duct 16 and in the right-hand area passes in continuously curved manner into the rising branch of the siphon 20.

Virtually parallel and closely adjacent to the rising branch of the siphon 20 an aerating duct 18 coming roughly vertically from above is connected in communicating manner with the measuring chamber 14 in the vicinity of the transmission to the siphon 20. This aerating duct 18 passes into a much wider back flow duct 51 and which consequently has a much larger air volume and which in the upper area significantly exceeds the top level of the siphon 20. This back flow duct 51 has at its narrowest point roughly three times the width of the duct of the measuring chamber 14 or the siphon 20. In the embodiment according to FIG.5 the outflow duct 26 issues in an inclined surface into a lower widening area of the back flow duct 51, which at the lower edge of the block 12 has an outflow opening 52, e.g. for the connection of a micturition bag.

In the sectional representation according to FIG. 6 along the section line A—A according to FIG. 5 the size of the back flow duct 51 compared with the diameter of the siphon 20 is clearly apparent. The back flow duct 51 used as an aerating and air return duct, has a much larger volume than the measuring chamber and siphon unit together.

The advantage of this embodiment of the siphon unit 50 is in particular that the aerating duct 18 is supplied back internally from the outflow duct 26, via the back flow duct 51, to the measuring chamber. Thus, there is only one inflow opening 53 and one outflow opening 52, so that in the intensive care unit there is no need for bacterial filters for avoiding contamination via the aerating duct. The volume relationship makes it clear that the volume of the measuring chamber and the siphon 20 is reduced to a minimum, so that the subdivided measuring volumes of the outflowing liquid can be digitally determined. Even in the case of an abrupt outflow of said small measuring volumes it is possible to ensure a rapid pressure compensation through the large volume nature of the back flow duct 51. Moreover, even in the case of relatively strong micturition, it is ensured that the measuring chamber 14 and the siphon 20 can be emptied in pulse-like manner and without any retention into the outflow or discharge duct 26, because in the upper area of the back flow duct 51 there is a collecting volume for larger liquid quantities occuring in surge-like manner.

FIG. 7 shows another embodiment of a somewhat modified siphon unit 50, but is comparable with that of FIG. 5 with regards to the basic principle of the measuring chamber and the siphon 20.

Unlike in the case of e.g. FIG. 5, the filling duct 58 in FIG. 7 is constructed as a sloping duct, which continuously passes into the starting area of the measuring chamber 14, preferably above the top level of the siphon 20. As a result of this sloping duct 58 the liquid to be measured flows along the lower wall of said sloping duct, so that the air in the upper part of said duct can escape, thereby avoiding air inclusions, which would lead to a falsification of the coinciding measuring volumes to be measured.

In addition, in the embodiment according to FIG. 7, the vertically downwardly directed area of the outflow duct 26 is provided with a trumpet-shaped widening 56. This widening prevents drop formation in the outlet area and the aerohydrodynamics are improved particularly with a view to an accelerated outflow.

A diameter jump 24 (FIG. 1), which leads to an improvement of the liquid meniscus and therefore to a more accurate release characteristic, can e.g. also be provided in the inlet zone to the measuring chamber 14, e.g. at the transition to the sloping duct 58.

The diagrammatic representation of FIG. 8 also shows the basic structure as for the embodiments of FIGS. 5 and 7. However, what is important here is the return of the back flow duct 51, via the aerating duct 18 with an opening 60 in the vicinity of the intake to the measuring chamber 14. the measuring chamber 14.

However, this embodiment more particularly illustrates in the case of high liquid flow rates, i.e. for example in the case of strong micturition, the advantage that the digitally determinable individual measuring volumes are always separated by the inclusion of an air bubble and can consequently also be individually determined. The return of the aerating duct 18 takes place at the top siphon level, so that at the end of a liquid column emptied via the measuring chamber 14 and the siphon 20 an air bubble is present. Therefore this embodiment ensures that a minor variance can also be achieved with high flow rates, so that the principle of air inclusions can be compared with a "string of pearls".

FIGS. 9 and 10 diagrammatically show another embodiment of a siphon unit. FIG. 9 which is a view of the inner face of a half-block 65 shows that the duct arrangement constituted by the filling duct, measuring chamber, siphon and outflow duct is formed by a preferably transparent hose 66, which is inserted in accurate fitting manner in a semicircular recess 67 (FIG. 10) between guide pins 68 corresponding to the optimized geometrical configuration.

FIG. 10 shows in plan view the assemblability of the two substantially complementary constructed half-blocks 65. The guide pins 68 for the insertion of the hose 66 simultaneously serve as connecting pins, which are insertable in the complementary bores 69 or depressions in an accurately fitting manner. The actual hose 66 is located in the semicircular recesses 67 of the corresponding half-block 65.

The essential advantage of this siphon unit 64 is that only the hose has to be replaced in the sense of a disposable article following use. However, the half-blocks 65 can be reused immediately or following sterilization, so that this embodiment leads to a significant cost saving.

FIG. 11 shows the electronic principle of the detector means 70, which contains corresponding correlation means for eliminating inclination or through-flow divergences. The microprocessor 71 receives signals via the measuring section block 73 with respect to the number of through-flowing measuring volumes and as a result the flow rate can also be determined. There is also a block 72, which as a clinometer gives the inclined position of the siphon unit to the microprocessor 71.

As the inclination arrangement of the overall siphon unit influences the volume of the corresponding liquid in the measuring chamber and the siphon, although only to a limited extent, a slope or inclination correction block 74 is provided in which, in the manner of a file or table, it is possible to pole the inclination compensation data as a function of the inclination angle. In a comparable manner a flow correction block 75 is connected to the microprocessor 71 for different flow quantities. In said table or file-based correction block 75 the correction data are available in pollable manner and can influence the measuring volume unit in the case of different flow quantities.

A block 76 is diagrammatically connected to the microprocessor 71, said block 76 comprising peripherals, such as displays, printers, alarms, etc. The block 77 can be connected as an actuator block for interrupting the liquid flow to the processor 71. This actuator can be operated, if e.g. there is a transportation or bed transfer of an intensive care patient with the siphon unit connected. In such cases it would also be possible by a horizontal arrangement in place of the operational vertical measuring arrangement to have a back flow of liquid or urine, but this is prevented by the interrupt actuator.

Thus, in extremely inexpensive manner, the invention permits a very accurate measurement of a liquid flow in a digitized form, the measurement ring chamber and the siphon having minimum volumes and in particular a diameter of approximately 4 mm or somewhat higher.

We claim:

1. A method for measuring a volume of a liquid flow in successive measuring cycles comprising the steps of:

passing the liquid flow into a siphon unit with an outlet, subdividing the liquid flow into identical, small, individual volume flows during each measuring cycle by a chamber positioned upstream of the siphon unit, discharging the individual volume flows via the outlet and entraining sediment by rapid and complete emptying of the chamber and the siphon unit during each measuring cycle, directly digitally detecting and numbering the individual volume flows for the total liquid flow volume, and providing rapid pressure equalization during each measuring cycle by internal air feedback between the outlet and an area upstream of the siphon unit.

2. A method according to claim 1, wherein the individual volume flows are detected optically.

3. A method according to claim 2, wherein the individual volume flows are detected optically in the outlet of the siphon unit.

4. An apparatus for measuring a volume of a liquid flow comprising:

a siphon unit provided with a siphon subdividing the liquid flow into individual measuring volumes;

a filling duct, an outflow duct and an aerating duct for the liquid flow;

digital detector means for detecting each individual measuring volume during an emptying cycle initiated by the siphon unit; and an evaluating device for evaluating a volume of the liquid flow from the number of emptying cycles and the individual measuring volumes;

said siphon unit including an approximately horizontal chamber provided, in flow direction, close to the siphon and communicating with the siphon so that each of the individual volumes is temporarily stored in the approximately horizontal chamber and the siphon;

wherein said filling duct and said aerating duct communicate with said approximately horizontal chamber;

said approximately horizontal chamber extends into an inlet portion of said siphon;

said approximately horizontal chamber and said siphon having approximately the same internal diameter; and said aerating duct feeding air in said volume of liquid flow internally back to said approximately horizant chamber.

5. An apparatus according to claim 4, wherein said approximately horizontal chamber and said siphon have the same internal diameter.

6. An apparatus according to claim 4, wherein said approximately horizontal chamber has a bottom with a gradient relative to an inlet of said siphon.

7. An apparatus according to claim 4, and further comprising correction means for correcting for inclination divergences and variations in a flow rate of liquid from the individual measuring volumes.

8. An apparatus according to claim 4, wherein said siphon unit, including the filling duct, the outlet duct and the aerating duct, is constructed from two transparent plastic half-blocks that are homologous with respect to a central sectional plane and sealed against one another.

9. An apparatus according to claim 4, wherein the siphon has a diameter of approximately 3.5 mm to 5 mm.

10. An apparatus according to claim 4, wherein the digital detector means has at least one sensor directed into an outlet of the siphon unit.

11. An apparatus according to claim 10, wherein the sensor is an optical sensor.

12. An apparatus according to claim 4, wherein the siphon has an overflow edge and an expanded diameter adjacent to the overflow edge.

13. An apparatus according to claim 4, wherein the outflow duct has a trumpet-shaped widening.

14. An apparatus according to claim 4, wherein said filling duct is connected to said siphon by a duct having a bottom bevel.

15. An apparatus according to claim 4, wherein surfaces of liquid carrying parts of the siphon unit and the approximately horizontal chamber are made from hydrophobic material.

16. An apparatus according to claim 4, wherein the siphon unit is made from a transparent biodegradable plastic and the digital detector means has a reflecting light barrier.

17. An apparatus according to claim 4, wherein the siphon unit is formed by two half-blocks and at least said filling duct and said outflow duct are formed by an interchangeable hose inserted between the two half-blocks, said two half-blocks being sealed against one another and constructed substantially homologously with respect to a central sectional plane.

18. An apparatus according to claim 4, wherein said volume of a liquid flow is a volume of urine flow.

* * * * *